(12) United States Patent
Yasukochi et al.

(10) Patent No.: US 8,173,155 B2
(45) Date of Patent: May 8, 2012

(54) ADHESIVE PATCH

(75) Inventors: Takashi Yasukochi, Ibaraki (JP);
Tetsuro Tateishi, Ibaraki (JP); Naruhito Higo, Ibaraki (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 1331 days.

(21) Appl. No.: 11/141,727

(22) Filed: May 31, 2005

(65) Prior Publication Data

US 2005/0266063 A1 Dec. 1, 2005

(30) Foreign Application Priority Data

Jun. 1, 2004 (JP) .................................. 2004-163286

(51) Int. Cl.
*A61F 13/02* (2006.01)

(52) U.S. Cl. .......................... 424/448; 424/449; 424/484

(58) Field of Classification Search ................. 424/449, 424/427

See application file for complete search history.

(56) References Cited

U.S. PATENT DOCUMENTS

| | | | | |
|---|---|---|---|---|
| 5,601,839 | A * | 2/1997 | Quan et al. ................. | 424/448 |
| 5,725,876 | A * | 3/1998 | Mantelle et al. ............. | 424/449 |
| 6,024,976 | A * | 2/2000 | Miranda et al. ............. | 424/449 |
| 6,596,401 | B1 * | 7/2003 | Terry et al. ................. | 428/447 |
| 2002/0004065 | A1 * | 1/2002 | Kanios ..................... | 424/449 |
| 2004/0001882 | A1 | 1/2004 | Tisa-Bostedt et al. | |
| 2004/0028724 | A1 * | 2/2004 | Terahara et al. ............ | 424/449 |
| 2004/0057985 | A1 | 3/2004 | Bracht | |
| 2004/0142024 | A1 * | 7/2004 | Chono et al. ............... | 424/449 |
| 2005/0260254 | A1 | 11/2005 | Breitenbach et al. | |

FOREIGN PATENT DOCUMENTS

| | | |
|---|---|---|
| CA | 2220358 A1 | 11/1996 |
| CA | 2336712 A1 | 1/2000 |
| EP | 1 340 496 A1 | 9/2003 |
| JP | 04-266818 | 9/1992 |
| JP | 04-266821 | 9/1992 |
| JP | 06-072864 | 3/1994 |
| JP | 06-327756 | 11/1994 |
| JP | 09-268275 A | 10/1997 |
| JP | 09-301854 | 11/1997 |
| JP | 11-012167 | 1/1999 |
| JP | 11-504643 T | 4/1999 |
| JP | 2002-520272 T | 7/2002 |
| WO | WO-01/32115 A1 | 5/2001 |
| WO | WO-01/35883 A1 | 5/2001 |
| WO | WO-02/069942 A1 | 9/2002 |
| WO | 2004/012721 A2 | 2/2004 |
| WO | WO-2004/019930 A1 | 3/2004 |
| WO | WO-2004/019987 A1 | 3/2004 |
| WO | WO-2004/019988 A1 | 3/2004 |

OTHER PUBLICATIONS

T. Kokubo et al., "Interaction Between Drugs and Pressure-Sensitive Adhesives in Transdermal Therapeutic Systems", Pharmaceutical Research, 11(1), pp. 104-107 (1994).

* cited by examiner

*Primary Examiner* — Michael G Hartley
*Assistant Examiner* — Micah-Paul Young
(74) *Attorney, Agent, or Firm* — Edwards Wildman Palmer LLP; Peter F. Corless; Nicholas J. DiCeglie, Jr.

(57) ABSTRACT

The present invention relates an adhesive patch comprising a backing layer and an adhesive layer that contains a drug, wherein the adhesive layer contains a mixed adhesive base containing a hydrocarbon rubber and a silicon-containing polymer. The adhesive patch of the invention shows extremely superior skin absorbability of a drug in a preparation, reduced skin irritation, and excellent aging stability of the drug in the preparation, and can achieve easiness of drug-taking methods and improvement in compliance.

20 Claims, 1 Drawing Sheet

ADHESIVE PATCH

TECHNICAL FIELD

The invention relates to an adhesive patch having an adhesive layer containing a drug and a mixed adhesive base that contains a hydrocarbon rubber and a silicon-containing polymer.

BACKGROUND ART

As an administration method of a drug, conventionally oral administration methods which use tablets, capsules and syrups are known; in recent years however, drug-administration methods using adhesive patches have been investigated. With a method using adhesive patches, various problems involved in oral administration methods are solved, and the method has several advantages including a reduction of the number of administrations, improvement in compliance, and easiness of administration and its discontinuation; therefore, it has been expected as an useful drug administration method for elderly and child patients.

However, when a conventional adhesive patch is used, because the cornified layer has extremely high fat solubility and low skin permeability of a drug in general, and the cornified layer of the normal skin has a barrier function to prevent invasion of foreign matters, in many cases a blended drug is not percutaneously absorbed sufficiently.

Therefore, to increase the skin absorbability of a drug in percutaneous administration using adhesive patches, various studies on composition, etc. of adhesive agents used in the adhesive patches have been carried out and, as a part of such studies, adhesive patches which use polymer materials such as an acrylic polymer or rubber polymer as an adhesive base have been proposed (refer to patent documents 1-6). However, even with these attempts, the skin absorbability of a drug blended in an adhesive patch is not sufficient, and further development of preparations having superior skin absorbability has been desired. In addition, preparations produced with conventional adhesive bases sometimes cause problems of skin irritation and aging instability of a drug blended in the adhesive patch, which leads to expectation of further improvement in terms of preparation.

Meanwhile, ambroxol, in particular ambroxol hydrochloride is known as an excellent expectant, and is widely used in clinical practices for respiratory diseases in which severe expectation is often observed. Conventionally, oral administration methods using tablets, liquid agents, syrups, dry syrups, and capsules have been widely adopted; however, decomposition and metabolism accompanying with oral administration cannot be avoided. In addition, expectation is known to become severe at the time of awakening early; accordingly, it is important for an expectant to be effective in early morning than during daytime. Nonetheless, because ambroxol has a short half life inside the body, if it is administered via a conventional oral administration method (tablet, syrup, etc.) after supper, sufficient blood concentration of ambroxol would not be obtained in early morning, resulting in insufficient exertion of the drug efficacy.

To solve such problems, sustained-release capsules have been developed, making it possible to maintain a high blood concentration continuously and to exert superior therapeutic effects compared with tablets, etc. However, it is still difficult for preparations other than sustained-release capsules to perform effective therapy; even sustained-release capsules have a disadvantage in terms of convenience of administration. That is, 70% of patients prescribed with an expectant are children and the elderly, and considering the swallowing difficulty of the elderly and body type of children, capsule dosage form is a difficult one for such patients to take. In addition, in the recent aging society, the number of elderly patients with decreased swallowing ability is increasing; thus, a preparation having a dosage form that is easy to take has been clinically desired.

In patent documents 7-9, tape preparations, adhesive agents and adhesive tapes for medical use are disclosed, in which ambroxol hydrochloride is described as a drug that may be used therein. However, in these documents, the name of ambroxol hydrochloride is only just mentioned without any specific formula, and therefore the disclosure in these documents is not sufficient from the practical viewpoint; whether or not an adhesive patch containing ambroxol hydrochloride as an effective preparation, that has sufficient skin absorbability to be used for actual therapy of patients, can be produced has not yet been clarified.

Furthermore, as an external preparation of expectant, a skin-absorption preparation containing bromhexine as an active component has been disclosed (patent document 10); however, a skin-absorption preparation containing ambroxol has not yet existed.

Patent document 1: JP, A, 4-266821
Patent document 2: JP, A, 9-301854
Patent document 3: WO2002/069942
Patent document 4: WO2004/019930
Patent document 5: WO2004/019987
Patent document 6: WO2004/019988
Patent document 7: JP No. 3132837
Patent document 8: JP No. 3192765
Patent document 9: JP No. 3233732
Patent document 10: JP, A, 11-12167

DISCLOSURE OF THE INVENTION

Problems to be Solved by the Invention

Consequently, the object of the invention is to provide an adhesive patch exhibiting very good skin absorbability of a drug contained in a preparation, reduced skin irritation and superior aging stability of the drug in the preparation, that can achieve easiness of administration and improvement in compliance. Furthermore, another object of the invention is to provide an ambroxol-containing adhesive patch that has sufficient skin absorbability to be actually used for therapy of patients.

Means to Solve the Problems

During extensive research to solve the above problems, the inventors found that, by blending a mixed adhesive base that contains a hydrocarbon rubber and a silicon-containing polymer, as well as a drug into an adhesive layer of an adhesive patch, a preparation having extremely superior skin absorbability of the drug and extremely superior physical properties in the adhesive patch, which shows reduced skin irritation with good aging stability of the drug in the preparation can be obtained; the inventors also found that the preparation shows significantly superior sustainability of the drug effects compared with conventional oral preparations, and achieves easiness of taking drugs and improvement in compliance; and the inventors completed the adhesive patch of the invention. The inventors further advanced the research, and found for the first time that by blending ambroxol into the adhesive patch of the invention, an adhesive patch containing ambroxol can be realized, and that this adhesive patch can exert very good percutaneous absorption of the ambroxol, and the inventors completed the invention.

Namely, the invention relates to an adhesive patch comprising a backing layer and an adhesive layer that contains a drug, wherein the adhesive layer contains a mixed adhesive base containing a hydrocarbon rubber and a silicon-containing polymer.

Further, the invention relates to the adhesive patch, wherein the hydrocarbon rubber is an ABA copolymer.

The invention further relates to the adhesive patch, wherein the ABA block copolymer is a stylene-isoprene-stylene block copolymer and/or a stylene-butadiene-stylene block copolymer.

Further, the invention also relates to the adhesive patch, wherein the ABA block copolymer is a stylene-isoprene-stylene block copolymer.

The invention also relates to the adhesive patch, wherein the silicon-containing polymer is a silicone that is partially endcapped with a trimethyl silyl group.

Further, the invention relates to the adhesive patch, wherein the silicon-containing polymer is polydimethyl siloxane.

Further, the invention relates to the adhesive patch, wherein the mixture ratio of the hydrocarbon rubber and the silicon-containing polymer is 10:1 to 10:120.

Further, the invention relates to the adhesive patch, wherein the drug is ambroxol and/or its pharmaceutically acceptable salts.

Effect of the Invention

In an adhesive patch of the invention, by blending a drug and a mixed adhesive base containing a hydrocarbon rubber and a silicon-containing polymer in an adhesive layer of the adhesive patch, the skin permeability of the drug blended in the adhesive patch is significantly improved compared with an adhesive patch utilizing a conventional adhesive base, thus achieving a preparation having extremely superior skin absorbability; accordingly, the effects of the drug blended in the adhesive patch can be sufficiently exerted.

Furthermore, an adhesive patch of the invention exhibits superior physical properties, reduced skin irritation, and excellent aging stability of a drug within a preparation; thus the invention can provide a drug-containing adhesive patch with a high level of safety. In addition, when a drug which was conventionally administered as an oral preparation is administered via the adhesive patch of the invention, the drug can be administered as a preparation with significantly superior sustainability of the drug efficacy, without being subjected to decomposition in the digestive organs and metabolism in the liver, etc., thus, the adhesive patch of the invention can simplify conventional drug-taking methods and improve compliance.

Moreover, by blending ambroxol as a drug to the adhesive patch of the invention, an ambroxol-containing adhesive patch having the above-mentioned effects can be provided. Namely, an ambroxol-containing expectrant preparation of the invention has superior skin permeability, and therefore the ambroxol-containing expectrant preparation with extremely superior skin absorbability that may improve conventional-drug-taking methods and compliance can be provided.

That is, the adhesive patch of the invention exhibits superior physical properties, reduced skin irritation and superior aging stability of a drug blended in a preparation, with which the drug blended in the adhesive patch is percutaneously absorbed sufficiently to show sufficient drug efficacy; furthermore, by blending ambroxol into the adhesive patch, an ambroxol-containing adhesive patch having the above-mentioned effects can be realized. The adhesive patch having such effects was realized for the first time by this invention.

BEST EMBODIMENT FOR CARRYING OUT THE INVENTION

In the following, embodiments of the invention is illustrated in detail.

The adhesive patch of the invention is one in which a backing layer, an adhesive layer and a release liner layer are sequentially laminated, wherein in at least one kind of drug and a mixed adhesive base that contains a hydrocarbon rubber and a silicon-containing polymer are blended in the adhesive layer as essential components.

The hydrocarbon rubber used in the adhesive patch of the invention is not particularly limited, as long as it is a polymer of formula $C_nH_m$ (n and m are independently of each other n=20-10000, m=20-10000). Hydrocarbon rubber used in the invention includes stylene-isoprene-stylene block copolymer (hereafter abbreviated as SIS), isoprene rubber, polyisobutylene (hereafter abbreviated as PIB), stylene-butadiene-stylene block copolymer (hereafter abbreviated as SBS), and stylene-butadiene rubber (hereafter abbreviated as SBR); among them, an ABA block copolymer is preferred SIS and PIB are more preferred, and SIS is the most particularly preferred. Such hydrocarbon rubbers may be used alone, or as a mixture of two or more kinds thereof.

The blended amount of the above-mentioned hydrocarbon rubber in the adhesive patch of the invention is not particularly limited; however, from the viewpoint of formation of an adhesive layer and skin permeability, preferably it is 5-90 wt. %, more preferably 10-70 wt. %, and most preferably 10-50 wt. %, based on the total amount of the preparation.

The silicon-containing polymer used in the adhesive patch of the invention is not particularly limited, as long as it favorably affects skin absorbability of the drug by forming a mixed adhesive base with hydrocarbon rubber. Namely, general medical-grade silicone type adhesive agents may be used; among them, a silicone that is partially endcapped with one or more trimethyl silyl groups is preferred, and polydimethyl siloxane is particularly preferred. This is because, by reducing the content of residual silanol group in the silicone, an increase in the drug release characteristic from the preparation can be expected by weakening the interaction with the drug. In this specification, "partially endcapped with one or more trimethyl silyl groups" means that at least one silanol group in the silicone is endcapped with a trimethyl silyl group.

Examples of polydimethyl siloxane which is a silicone partially endcapped with a trimethyl silyl group include pressure-sensitive adhesive agents manufactured by Dow Corning, such as BIO-BSA X7-4201, BIO-BSA X7-2960, BIO-BSA X7-3027, BIO-BSA X7-2910, BIO-BSA X7-4820, BIO-BSA X7-2892, BIO-BSA X7-2994, BIO-BSAX7-3019, BIO-BSA Q7-2920, etc.; in particular, BIO-BSAX7-4201 pressure-sensitive adhesive agent manufactured by Dow Corning is especially preferred. Such silicon-containing polymers may be used alone, or as a mixture of two or more kinds thereof.

The blended amount of the above-mentioned silicon-containing polymer in the adhesive patch of the invention is not particularly limited; however, from the viewpoint of formation of an adhesive layer and skin permeability, preferably it is 3-90 wt. %, more preferably 5-60 wt. %, and most preferably 10-30 wt. %, based on the total amount of the preparation.

The mixture ratio of the hydrocarbon rubber to silicon-containing polymer in the adhesive base layer of the adhesive patch of the invention is not particularly limited; however, from the viewpoint of physical properties of a preparation and skin permeability of a drug, preferably it is 10:1 to 10:120, more preferably 10:1 to 10:20, and most preferably 3:4.

Furthermore, as a base for the adhesive layer of the adhesive patch of the invention, an acrylic polymer may be blended in addition to the above essential components. The acrylic polymer is not particularly limited, as long as it is one that is copolymerized with at least one (meth)acrylate derivatives represented by 2-ethylhexyl acrylate, methyl acrylate, butyl acrylate, hydroxyethyl acrylate, 2-ethylhexyl methacrylate, etc. Examples that may be used include those described in "Encyclopedia of pharmaceutical additives 2000 (edited by Japan Pharmaceutical Additive Association)" as adhesive agents, such as copolymer of acrylic acid/octyl acrylate ester, copolymer solution of 2-ethylhexyl acrylate/vinyl pyrrolidone, copolymer of acrylic ester/vinyl acetate, copolymer of 2-ethylhexyl acrylate/2-ethylhexyl methacrylate/dodecyl methacrylate, copolymer resin emulsion of methyl acrylate/2-ethylhexyl acrylate, acrylic polymer adhesive agents containing a solution of acryl resin alkanol amine, Duro-Tak acryl adhesive series (manufactured by National Starch & Chemical Company), and EUDRAGIT series (from Higuchi Shokai Co., Ltd.).

The drug used in the adhesive patch of the invention is not particularly limited, as long as it can improve the skin absorbability when used in the mixed adhesive base containing the above hydrocarbon rubber and silicon-containing polymer; however, ambroxol and/or its pharmaceutically acceptable salts are particularly preferred. Here, the pharmaceutically acceptable salts are not particularly limited, and they may be either inorganic salts or organic salts. In particular, ambroxol hydrochloride which is a representative salt of ambroxol is especially preferred.

It is preferred that ambroxol and/or its pharmaceutically acceptable salts are blended with 0.5-50 wt. % based on the total amount of the preparation, from the viewpoint of physical properties and skin absorbability of the preparation.

Further, the adhesive layer of the adhesive patch of the invention may contain a plasticizer. Plasticizers which may be used include petroleum oil (e.g., paraffinic processed oil, napthenic processed oil, aromatic processed oil, etc.), squalane, squalene, vegetable oil (e.g., olive oil, camellia oil, caster oil, tall oil, arachis oil), silicon oil, dibasic acid ester (e.g., dibutyl phthalate, dioctyl phthalate, etc.), liquid rubber (e.g., polybutene, liquid isoprene rubber), liquid fatty acid ester (isopropyl myristate, hexyl laurate, diethyl sebaciate, diisopropyl sebaciate), diethylene glycol, polyethylene glycol, glycol salicylate, propylene glycol, dipropylene glycol, triacetin, triethyl citrate, crotamiton, etc.; among them, liquid paraffin, liquid polybutene, isopropyl myristate, diethyl sebaciate, and hexyl laurate are particularly preferred.

These plasticizers may be used alone, or as a mixture of two or more kinds thereof. Such plasticizers may be blended, in total, at a ratio of 5-70 wt. %, preferably 5-60 wt. %, and more preferably 10-50 wt. %, based on the entire composition of the adhesive layer, with consideration given to sufficient skin permeability of a drug and maintenance of sufficient cohesive force as an adhesive-patch preparation.

When the adhesive force is not sufficient in the adhesive layer of the adhesive patch of the invention, it is desirable that a tackifier resin is further blended. Tackifier resins that can be used include rosin derivatives (e.g., rosin, glycerin esters of rosin, hydrogenated rosins, glycerin esters of hydrogenated rosin, pentaerythritol esters of rosin, etc.), saturated alicyclic hydrocarbon resins (e.g., ARKON P-100, Arakawa Chemical Industries, Ltd.), aliphatic hydrocarbon resins (e.g., Quintone B170, Zeon Corporation), terpene resins (e.g., Clearon P-125, Yasuhara Chemical), maleic acid resins and the like. Particularly preferred tackifier resins include glycerin esters of hydrogenated rosin, saturated alicyclic hydrocarbon resins, aliphatic hydrocarbon resins, and terpene resins.

Such a tackifier resin may be blended, at a ratio of 5-70 wt. %, preferably 5-60 wt. %, and more preferably 10-50 wt. %, based on the entire composition of the adhesive layer, with consideration given to sufficient adhesive force and irritation to skin upon releasing as an adhesive patch.

In the adhesive layer of the adhesive patch of the invention, an absorption enhancer may be contained. As the absorption enhancer, any heretofore known compounds of which an absorption enhancing effect on the skin is known may be used. Examples include $C_6$-$C_{20}$ fatty acids, fatty alcohols, fatty acid esters, amides, or ethers, aromatic organic acids, aromatic alcohols, aromatic organic acid esters or ethers (those heretofore described may be either saturated or unsaturated, and either cyclic, straight chain or branched chain), furthermore, lactic acid esters, acetic acid esters, monoterpene compounds, sesquiterpene compounds, Azone, Azone derivatives, pyrothiodecane, glycerin fatty acid esters, propylene glycol fatty acid esters, sorbitan fatty acid esters (Span), polysorbates (Tween), polyethlene glycol fatty acid esters, polyoxyethylene hardened castor oils (HCO), polyoxyethylene alkyl ethers, sucrose fatty acid esters, vegetable oils and the like.

As examples of an absorption enhancer, caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methy laurate, hexyl laurate, lauric diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerol monocapryrate, glycerol monocaprate, glycerol monolaurate, glycerol monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pyrothiodecane, and olive oil are preferred; in particular, lauryl alcohol, isostearyl alcohol, lauric diethanolamide, glycerol monocapryrate, glycerol monocaprate, glycerol monooleate, sorbitan monolaurate, propylene glycol monolaurate, polyoxyethylene lauryl ether, and pyrothiodecane are preferred.

Such absorption enhancers may be used alone, or as a mixture of two or more kinds thereof. The content of absorption enhancers is preferably 0.01-20 wt. %, more preferably 0.05-10 wt. % and most preferably 0.1-5 wt. % based on the entire composition of the adhesive layer, with consideration given to skin permeability and skin irritation such as rub or and edema as an adhesive patch.

In the invention, when the drug is a pharmaceutically acceptable acid addition salt, it is preferred that an organic acid is further contained in the adhesive layer. Organic salts that can be used include aliphatic (mono-, di- or tri-)carboxylic acids (e.g., acetic acid, propionic acid, isobutylic acid, caproic acid, caprylic acid, lactic acid, maleic acid, pyruvic acid, oxalic acid, succinic acid, tartaric acid, etc.), aromatic carboxylic acids (e.g., phthalic acid, salicylic acid, benzoic acid, acetyl salicylate, etc.), alkyl sulfonates (e.g., methane sulfonate, ethane sulfonate, propyl sulfonate, butane sulfonate, polyoxyethylene alkyl ether sulfonate, etc.), alkyl sulfonate derivatives (e.g., N-2-hydroxyethyl piperidine-N'-2-ethane sulfonate (hereafter abbreviated as "HEPES"), etc.), and cholic acid derivatives (e.g., dehydro cholic acid, etc.); among them, acetic acid, propionic acid, lactic acid and salicylic acid are preferred, and acetic acid is most preferred. Salts of these organic acids as well as their mixtures may also be used.

The content of these organic acids is preferably 0.01-20 wt. %, more preferably 0.1-15 wt. % and most preferably 0.1-10 wt. % based on the entire composition of the adhesive layer, from the view point of sufficient skin permeability and skin irritation as an adhesive patch.

Furthermore, if necessary, other agents such as an antioxidant, filler, cross-linking agent, preservative and ultraviolet absorber may be blended in the adhesive patch of the invention. As antioxidants, tocopherol and its ester derivatives, ascorbic acid, ascorbic acid-stearic acid ester, nordihydroguaretic acid, dibutyl hydroxy toluene (BHT), butyl hydroxy anisole and the like are preferable. As fillers, calcium carbonate, magnesium carbonate, silicates (e.g., aluminum silicate, magnesium silicate, etc.), silicic acid, barium sulfate, calcium sulfate, calcium plumbite, zincoxide, titanium oxide and the like are preferable. As cross-linking agents, thermosetting resins such as amino resins, phenol resins, epoxy resins, alkyd resins and unsaturated polyesters, isocyanate compounds, block isocyanate compounds, organic cross-linking agents, and inorganic cross-linking agents such as metals or metal compounds are preferable. As preservatives, ethyl p-hydroxybenzoate, propyl p-hydroxybenzoate, butyl p-hydroxybenzoate and the like are preferable. As ultraviolet absorbers, p-aminobenzoic acid derivatives, anthranilic acid derivatives, salicylic acid derivatives, coumarin derivatives, amino-acid compounds, imidazoline derivatives, pyrimidine derivatives, dioxane derivatives and the like are preferable.

Such an antioxidant, filler, cross-linking agent, preservative and ultraviolet absorber may be blended with, preferably 10 wt. % or less, more preferably 5 wt. % or less, and most preferably 2 wt. % or less, based on the entire composition of the adhesive layer of the adhesive patch.

An adhesive patch of the invention that contains an adhesive layer with the above composition containing a drug may be appropriately prepared; for example, it can be obtained as follows: components of an adhesive base containing a drug are dissolved in a solvent such as toluene, hexane and ethyl acetate, and the mixture is extended on a release liner or a backing and the solvent is removed by drying, then the resultant is attached to the backing or the release liner. However, an adhesive patch of the invention cannot be prepared by a hot-melt method.

The backing layer of the adhesive patch of the invention is not particularly limited as long as it is appropriate for supporting the adhesive layer; a stretch or nonstretch material may be used. For example, fabric, non-woven fabric, polyurethane, polyester, polyvinyl acetate, polyvinylidene chloride, polyethylene, polyethylene terephthalate, aluminum sheet, etc., or composite materials thereof may be used.

As the release liner of the adhesive patch of the invention, in concrete terms, films such as polyesters (e.g. polyethylene terephthalate)polyvinyl chloride and polyvinylidene chloride, a laminated film of high-quality paper with polyolefin, and the like may be used. In such a release liner layer, to facilitate operation of releasing the release liner from the adhesive side, a fluorine treatment is preferably applied to the release liner at the side attached to the adhesive layer.

In the following, the invention is explained in more detail by examples. The invention, however, is not limited to these examples, and the sequence of blending of each component is not particularly limited. Furthermore, various modifications may be possible without departing from the technical idea of the invention. Here, in the examples, "%" means "wt. %" unless otherwise specified.

EXAMPLE 1

| | |
|---|---|
| SIS | 15.4% |
| Silicon-containing polymer (BIO-BSA X7-4201, Dow Corning) | 20.5% |
| Saturated alicyclic hydrocarbon resin (ARKON P-100, Arakawa Chemical Industries, Ltd.) | 46.1% |
| Isopropyl myristate (IPM) | 5.0% |
| Pyrothiodecane | 3.0% |
| Ambroxol | 10.0% |
| Total | 100.0% |

Ambroxol, pyrothiodecane and isopropyl myristate (IPM) were well mixed previously, then mixed with the remaining components dissolved in toluene. The mixture was coated on a release liner and the solvent was removed by drying, then the liner was attached to a backing to obtain the adhesive patch of the invention.

EXAMPLE 2

| | |
|---|---|
| SIS | 13.5% |
| Silicon-containing polymer (BIO-BSA X7-4201, Dow Corning) | 18.0% |
| Saturated alicyclic hydrocarbon resin (ARKON P-100, Arakawa Chemical Industries, Ltd.) | 40.5% |
| Isopropyl myristate | 5.0% |
| Pyrothiodecane | 3.0% |
| Ambroxol | 20.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the invention.

EXAMPLE 3

| | |
|---|---|
| SIS | 11.6% |
| Silicon-containing polymer (BIO-BSA X7-4201, Dow Corning) | 15.5% |
| Saturated alicyclic hydrocarbon resin (ARKON P-100, Arakawa Chemical Industries, Ltd.) | 34.9% |
| Isopropyl myristate | 5.0% |
| Pyrothiodecane | 3.0% |
| Ambroxol | 30.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the invention.

EXAMPLE 4

| | |
|---|---:|
| SIS | 9.75% |
| Silicon-containing polymer (BIO-BSA X7-4201, Dow Corning) | 13.0% |
| Saturated alicyclic hydrocarbon resin (ARKON P-100, Arakawa Chemical Industries, Ltd.) | 29.25% |
| Isopropyl myristate | 5.0% |
| Pyrothiodecane | 3.0% |
| Ambroxol | 40.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the invention.

COMPARATIVE EXAMPLE 1

| | |
|---|---:|
| Silicon-containing polymer (BIO-BSA X7-4201, DowCorning) | 72.0% |
| Isopropyl myristate | 5.0% |
| Pyrothiodecane | 3.0% |
| Ambroxol | 20.0% |
| Total | 100.0% |

Ambroxol, pyrothiodecane and isopropyl myristate were well mixed previously, then mixed with a silicon-containing polymer. The mixture was coated on a release liner and the solvent was removed by drying, then the liner was attached to a backing layer to obtain the adhesive patch of the comparative example.

COMPARATIVE EXAMPLE 2

| | |
|---|---:|
| SIS | 20.5% |
| Saturated alicyclic hydrocarbon resin (ARKON P-100, Arakawa Chemical Industries, Ltd.) | 61.5% |
| Isopropyl myristate | 5.0% |
| Pyrothiodecane | 3.0% |
| Ambroxol | 10.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the comparative example.

COMPARATIVE EXAMPLE 3

| | |
|---|---:|
| SIS | 18% |
| Saturated alicyclic hydrocarbon resin (ARKON P-100, Arakawa Chemical Industries, Ltd.) | 54% |
| Isopropyl myristate | 5.0% |
| Pyrothiodecane | 3.0% |
| Ambroxol | 20.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the comparative example.

COMPARATIVE EXAMPLE 4

| | |
|---|---:|
| SIS | 15.5% |
| Saturated alicyclic hydrocarbon resin (ARKON P-100, Arakawa Chemical Industries, Ltd.) | 46.5% |
| Isopropyl myristate | 5.0% |
| Pyrothiodecane | 3.0% |
| Ambroxol | 30.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the comparative example.

COMPARATIVE EXAMPLE 5

| | |
|---|---:|
| SIS | 13.0% |
| Saturated alicyclic hydrocarbon resin (ARKON P-100, Arakawa Chemical Industries, Ltd.) | 39.0% |
| Isopropyl myristate | 5.0% |
| Pyrothiodecane | 3.0% |
| Ambroxol | 40.0% |
| Total | 100.0% |

Ambroxol, pyrothiodecane and isopropyl myristate were well mixed previously, then mixed with the remaining components dissolved in toluene. The mixture was coated on a release liner and the solvent was removed by drying, then the liner was attached to a backing to obtain the adhesive patch of the comparative example.

COMPARATIVE EXAMPLE 6

| | |
|---|---|
| Acrylic polymer (SK dyne MAS811, Soken Kagaku) | 80.0% |
| Ambroxol | 20.0% |
| Total | 100.0% |

Ambroxol and the acrylic polymer were mixed and stirred previously. The mixture was coated on a release liner and the solvent was removed by drying, then the liner was attached to a backing to obtain the adhesive patch of the comparative example.

TEST EXAMPLE

Skin Permeability Test Using Hairless Mouse

The skin of a hairless mouse was removed from the back, and then with its dermal side exposed to the receptor-layer side, the skin was mounted on a flow-through cell (5 $cm^2$), the circumferential part of which 37° C. warm water was circulated. The preparations obtained from examples 1-4 and comparative examples 1-6 were attached to the skin's cornified-layer side; using saline in the receptor layer, sampling was carried out every 2 h until 24 h at a rate of 5 ml/h. At each sampling time, for each of the receptor solution obtained, the flow volume was accurately measured, the drug concentration was measured by high-performance liquid chromatography, and the drug permeating rate per hour was calculated to determine the skin permeating rate of the drug per unit area in the static state. It is recognized that the larger the skin permeating rate, the higher the skin absorbability. Table 1 shows the results.

NOTE) This preparation could not be subjected to the skin permeability test due to cohesive destruction.

As is obvious from the results shown in Table 1, when comparing the preparations of each of the examples of the invention with those of the comparative examples in which the same amount of the drug as that of the preparations in the examples of the invention is contained, the preparations obtained in the examples of the invention show approximately 1.5 times higher skin permeability of the drug than those obtained in the comparative examples, thus demonstrating that the adhesive patch of the invention is a preparation with an extremely superior skin absorbability. Furthermore, because the preparation of the comparative example 1 developed cohesive destruction and showed a problem in its physical properties, it is demonstrated that the adhesive patch of the invention is a preparation with extremely superior physical properties.

Therefore, compared with an adhesive patch using a conventional adhesive base, it is understood that the adhesive patch of the invention is the one wherein the skin absorbability of a drug blended in the adhesive patch is significantly improved, with excellent physical properties as well as superior aging stability of the drug in the preparation. Furthermore, the adhesive patch of the invention is demonstrated to be the preparation having extremely superior skin absorbability that can exert sufficient drug efficacy, as an ambroxol-containing adhesive patch.

INDUSTRIAL APPLICABILITY

As explained above, according to the invention, it becomes possible to provide an adhesive patch with extremely superior skin absorbability of a drug in a preparation, excellent physical properties, reduced skin irritation, and excellent aging stability of the drug in the preparation; therefore, the adhesive patch of the invention is expected to be applied as a pharmaceutical agent that can achieve easiness of drug-taking methods and improvement in compliance. Moreover, the invention

TABLE 1

| | | | Composition ratio (%) | | | Composition ratio of each base (%) | | | Skin permeability | Accumulated amount of Permeated |
| | | Adhesive base | Ambroxol | Pyrothiodecane | Isopropyl myristate | Hydrocarbon rubber (SIS) | Silicon-Containing Polymer | Saturated Alicyclic hydrocarbon resin (ARKON) | rate of drug μg/$cm^2$/h | drug μg/$cm^2$ |
|---|---|---|---|---|---|---|---|---|---|---|
| Example | 1 | Hydrocarbon | 10 | 3 | 5 | 15.4 | 20.5 | 46.1 | 16.3 | 324.3 |
| | 2 | rubber | 20 | 3 | 5 | 13.5 | 18.0 | 40.5 | 26.2 | 511.3 |
| | 3 | (SIS)/ | 30 | 3 | 5 | 11.6 | 15.5 | 34.9 | 36.5 | 722.9 |
| | 4 | silicon-containing polymer (BIO-BSA X7-4201) | 40 | 3 | 5 | 9.8 | 13.0 | 29.3 | 50.6 | 996.5 |
| Comparative example | 1 | Silicon-containing polymer (BIO-BSA X7-4201)$^{NOTE}$ | 20 | 3 | 5 | — | 72.0 | — | — | — |
| | 2 | Hydrocarbon | 10 | 3 | 5 | 20.5 | — | 61.5 | 9.8 | 185.8 |
| | 3 | rubber | 20 | 3 | 5 | 18.0 | — | 54.0 | 16.6 | 331.6 |
| | 4 | (SIS) | 30 | 3 | 5 | 15.5 | — | 46.5 | 27.7 | 538.3 |
| | 5 | | 40 | 3 | 5 | 13.0 | — | 39.0 | 42.8 | 850.4 |
| | 6 | Acrylic polymer (SK dyne) | 20 | — | — | — | — | — | 15.9 | 317.0 | can provide an ambroxol-containing adhesive patch with superior skin absorbability that can be used for therapy of patients.

BRIEF DESCRIPTION OF THE DRAWINGS

FIG. 1 shows a cross-sectional drawing of a structure of an adhesive patch of the invention.

DESCRIPTION OF SYMBOLS

1: Backing layer
2: Adhesive layer containing a drug
3: Release liner layer

The invention claimed is:

1. An adhesive patch consisting essentially of a backing layer and an adhesive layer, wherein:
said adhesive layer consists of:
(i) 10 to 40 wt % ambroxol or a pharmaceutically acceptable salt thereof,
(ii) 9.8 to 15.4 wt % of a hydrocarbon rubber selected from styrene-isoprene-styrene block copolymer and a styrene-butadiene-styrene block copolymer,
(iii) 13.0 to 20.5 wt % of polydimethyl siloxane,
(iv) 5 wt % of at least one plasticizer,
(v) 3 wt % of at least one absorption enhancer, and
(vi) 29.3 to 46.1 wt % of at least one tackifier resin;
and wherein the skin permeability rate of ambroxol is at least 16.3 $\mu g/cm^2/h$.

2. The adhesive patch according to claim 1, wherein the hydrocarbon rubber is a styrene-isoprene-styrene block copolymer.

3. The adhesive patch according to claim 1, wherein the skin permeability rate of ambroxol is 16.3 to 50.6 $\mu g/cm^2/h$.

4. The adhesive patch according to claim 1, wherein the cumulative skin permeation of ambroxol for 24 hours is at least 324 $\mu g/cm^2$.

5. An adhesive patch consisting essentially of a backing layer and an adhesive layer wherein:
said adhesive layer consists of:
(i) 10 to 40 wt % ambroxol or a pharmaceutically acceptable salt thereof,
(ii) 9.8 to 15.4 wt % of a hydrocarbon rubber selected from styrene-isoprene-styrene block copolymer and a styrene-butadiene-styrene block copolymer,
(iii) 13 to 20.5 wt % of polydimethyl siloxane,
(iv) 5 to 60 wt % of at least one plasticizer,
(v) 0.01 to 20 wt % of at least one absorption enhancer, and
(vi) 29.3 to 46.1 wt % of at least one tackifier resin.

6. The adhesive patch according to claim 5, wherein the at least one plasticizer is isopropyl myristate and the at least one absorption enhancer is pyrothiodecane.

7. The adhesive patch according to claim 6, wherein the content of isopropyl myristate is 5 wt %, and the content of pyrothiodecane is 3 wt %.

8. The adhesive patch according to claim 5, wherein the at least one tackifier resin is saturated alicyclic hydrocarbon resin.

9. The adhesive patch according to claim 5, wherein the hydrocarbon rubber is a styrene-isoprene-styrene block copolymer.

10. The adhesive patch according to claim 5, wherein the at least one absorption enhancer is present at 0.1 to 5 wt %.

11. An adhesive patch consisting essentially of a backing layer and an adhesive layer, wherein:
said adhesive layer consists of:
(i) 10 to 40 wt % ambroxol or a pharmaceutically acceptable salt thereof,
(ii) 9.8 to 15.4 wt % of a hydrocarbon rubber selected from styrene-isoprene-styrene block copolymer and a styrene-butadiene-styrene block copolymer,
(iii) 13.0 to 20.5 wt % of polydimethyl siloxane,
(iv) 5 wt % of at least one plasticizer,
(v) 3 wt % of at least one absorption enhancer,
(vi) 29.3 to 46.1 wt % of at least one tackifier resin, and
(vii) at least one other agent selected from the group consisting of antioxidant, filler, cross-linking agent, preservative and ultraviolet absorber;
and wherein the skin permeability rate of ambroxol is at least 16.3 $\mu g/cm^2/h$.

12. The adhesive patch according to claim 11, wherein the hydrocarbon rubber is a styrene-isoprene-styrene block copolymer.

13. The adhesive patch according to claim 11, wherein the skin permeability rate of ambroxol is 16.3 to 50.6 $\mu g/cm^2/h$.

14. The adhesive patch according to claim 11, wherein the cumulative skin permeation of ambroxol for 24 hours is at least 324 $\mu g/cm^2$.

15. An adhesive patch consisting essentially of a backing layer and an adhesive layer, wherein:
said adhesive layer consists of:
(i) 10 to 40 wt % ambroxol or a pharmaceutically acceptable salt thereof,
(ii) 9.8 to 15.4 wt % of a hydrocarbon rubber selected from styrene-isoprene-styrene block copolymer and a styrene-butadiene-styrene block copolymer,
(iii) 13 to 20.5 wt % of polydimethyl siloxane,
(iv) 5 to 60 wt % of at least one plasticizer,
(v) 0.01 to 20 wt % of at least one absorption enhancer,
(vi) 29.3 to 46.1 wt % of at least one tackifier resin, and
(vii) at least one other agent selected from a group consisting of antioxidant, filler, cross-linking agent, preservative and ultraviolet absorber.

16. The adhesive patch according to claim 15, wherein the at least one plasticizer is isopropyl myristate and the at least one absorption enhancer is pyrothiodecane.

17. The adhesive patch according to claim 16, wherein the content of isopropyl myristate is 5 wt %, and the content of pyrothiodecane is 3 wt %.

18. The adhesive patch according to claim 15, wherein the at least one tackifier resin is saturated alicyclic hydrocarbon resin.

19. The adhesive patch according to claim 15, wherein the hydrocarbon rubber is a styrene-isoprene-styrene block copolymer.

20. The adhesive patch according to claim 15, wherein the at least one absorption enhancer is present at 0.1 to 5 wt %.

* * * * *